(12) United States Patent
Ingerman et al.

(10) Patent No.: US 8,254,656 B2
(45) Date of Patent: Aug. 28, 2012

(54) METHODS AND SYSTEM FOR SELECTIVE RESOLUTION IMPROVEMENT IN COMPUTED TOMOGRAPHY

(75) Inventors: Eugene Alex Ingerman, San Francisco, CA (US); Samit Basu, Fremont, CA (US); Jed Pack, Glenville, NY (US); Todd Gable, Newark, CA (US)

(73) Assignee: Morpho Detection, Inc., Newark, CA (US)

( * ) Notice: Subject to any disclaimer, the term of this patent is extended or adjusted under 35 U.S.C. 154(b) by 549 days.

(21) Appl. No.: 12/578,196

(22) Filed: Oct. 13, 2009

(65) Prior Publication Data

US 2011/0085718 A1     Apr. 14, 2011

(51) Int. Cl.
*G06K 9/00* (2006.01)
*G01N 23/04* (2006.01)

(52) U.S. Cl. .............................. 382/131; 378/4; 378/57

(58) Field of Classification Search ................... 382/131; 378/4, 57

See application file for complete search history.

(56) References Cited

U.S. PATENT DOCUMENTS

| | | | |
|---|---|---|---|
| 5,825,908 A * | 10/1998 | Pieper et al. | 382/131 |
| 6,324,243 B1 * | 11/2001 | Edic et al. | 378/4 |
| 6,574,299 B1 | 6/2003 | Katsevich | |
| 6,922,457 B2 * | 7/2005 | Nagata et al. | 378/19 |
| 7,881,426 B2 * | 2/2011 | Basu et al. | 378/20 |
| 2005/0031075 A1 | 2/2005 | Hopkins et al. | |

FOREIGN PATENT DOCUMENTS

WO     2008036463 A2     3/2008

* cited by examiner

*Primary Examiner* — Alexander H Taningco
(74) *Attorney, Agent, or Firm* — Armstrong Teasdale LLP

(57) ABSTRACT

A method and system for selective resolution improvement in computed tomography (CT) scanning. The method includes receiving scan data representative of a scanned object from a CT scanner and reconstructing the scan data using a first algorithm to create a first set of reconstructed data. A region of interest is identified within the first set of reconstructed data. A portion of the scan data corresponding to the region of interest is reconstructed using a second algorithm to create a second set of reconstructed data. The first set of reconstructed data and the second set of reconstructed data are combined to create combined reconstructed data.

20 Claims, 4 Drawing Sheets

METHODS AND SYSTEM FOR SELECTIVE RESOLUTION IMPROVEMENT IN COMPUTED TOMOGRAPHY

BACKGROUND OF THE INVENTION

1. Field of the Invention

The embodiments described herein relate generally to identifying a characteristic of an object and, more particularly, to identifying a CT value of an object in a container to facilitate detecting contraband concealed within the container.

2. Description of the Related Art

It is known to use computed tomography (CT) based explosive detection systems (EDS) to detect the presence of contraband. As used herein, the term "contraband" refers to any goods, such as an object and/or a material, that are unauthorized to possess, including, without limitation, explosives, weapons, drugs, and/or controlled substances. As described herein, contraband is contained within a container, such as a cargo container, a bag, a box, baggage, luggage, a carton, a crate, and/or any other suitable receptacle.

As is known, each 2D image slice is formed from a rectangular array of picture elements, or pixels. The numeric value of each pixel represents a CT value, which is an estimate of density. As used herein, a CT value is used as an estimate of density of a material, although the CT value is typically defined as an indication of an attenuation coefficient of the material rather than being a measure of the density of the material.

At least some known EDS CT systems use multi-row X-ray detectors that acquire a number of two-dimensional (2D) projections through the object while the object moves between the X-ray source and the detector. Some such systems use an image reconstruction algorithm that consists of selecting a number of 2D image slices and selecting (using an algorithm) detector data that allows reconstructing the CT density data in the 2D slices through a container. Such systems may be referred to as implementing "multi-slice" algorithms. For example, multi-slice algorithms include advanced single-slice rebinning (ASSR) and ray consistency reconstruction (RCR). Multi-slice algorithms are inexact algorithms and are known to produce lower image quality reconstruction than more exact methods, such as Katsevich helical 3D reconstruction.

In at least some known analysis methods, the analysis of each image slice includes segmenting, or grouping together, contiguous pixels into regions. Regions within the different 2D image slices are then compared and grouped into image objects representing physical objects within the container.

At least some other known CT reconstruction algorithm systems generate full volume data through the use of a cone beam reconstruction algorithm. Instead of interpolating projection data onto the 2D surfaces, as is done in a multi-slice algorithm, a cone beam algorithm reconstructs directly the full, three dimensional (3D) representation of a scanned container. As is known, the volume is represented in the volume data by volume elements, or voxels. The numeric value of each voxel is a CT value. Similar to the 2D image analysis method, during at least one known 3D image analysis of the volume data, contiguous voxels with a similar CT value are grouped together into image objects that represent characteristics, such as a size, a shape, and an approximate density, of a physical object within the container. Rules are applied to the measurements of the image object, such as a density, a volume, a mass, and/or a shape, to determine if the physical object is contraband and/or another item of interest.

Cone beam algorithms are known to produce higher quality (e.g., higher resolution) output at the expense of increased computing requirements. Specifically, cone beam reconstruction of a given object requires the execution of significantly more processor instructions than are required for multi-slice reconstruction of the same object. In some contexts (e.g., where real-time scanning is required), one may opt for multi-slice reconstruction, despite the lower quality output. Because some forms of contraband, such as sheet explosives, are difficult to detect with a multi-slice algorithm, an alarm is produced for containers having areas falling within a relatively broad target range of CT values. The use of such a broad target range increases the occurrence of false alarms and the attendant cost of manual inspection. Conversely, narrowing the target range increases the occurrence of false negatives and the risk that contraband will go undetected.

BRIEF SUMMARY OF THE INVENTION

In one aspect, a method is provided for computed tomography (CT) scanning of an object. The method includes acquiring scan data representative of a scanned object from a CT scanning system and reconstructing the scan data by a computer using a first algorithm to create a first set of reconstructed data. A region of interest is identified within the first set of reconstructed data. A portion of the scan data corresponding to the region of interest is reconstructed by the computer using a second algorithm to create a second set of reconstructed data. The first set of reconstructed data and the second set of reconstructed data are combined to create combined reconstructed data.

In another aspect, a method is provided for computed tomography (CT) based detection of contraband. The method includes defining a target range of CT values corresponding to contraband. Scan data representative of a scanned object is received by a computer from a CT scanning system. The scan data is reconstructed by the computer using a first algorithm to create a first set of reconstructed data, which includes a plurality of regions having a plurality of CT values. At least one region having a CT value within the target range is identified within the first set of reconstructed data. At least one portion of the scan data corresponding to one of the identified regions is reconstructed by the computer using a second algorithm to create at least one additional set of reconstructed data. The at least one additional set of reconstructed data includes a plurality of regions having a plurality of CT values. The at least one additional set of reconstructed data is inspected by the computer to detect a presence of potential contraband in the scanned object.

In still another aspect, a CT control system is provided for detecting contraband according to a first range of CT values and a second range of CT values. The control system includes a data acquisition system (DAS) configured to acquire, from a detector array, scan data representing a scanned object. The control system also includes an image reconstructor that is communicatively coupled to the DAS and configured to produce reconstructed data from the acquired scan data using a plurality of algorithms. The control system further includes a computer that is operatively coupled to the image reconstructor. The computer is configured to acquire from the image reconstructor a first set of reconstructed data produced from the acquired scan data using a first algorithm. The computer is also configured to identify within the first set of reconstructed data at least one region having a CT value within the first range of CT values. The computer is further configured to acquire from the image reconstructor a second set of reconstructed data corresponding to the at least one identified region. The second set of reconstructed data is produced from the acquired scan data using a second algorithm. The computer is also configured to identify within the second set of reconstructed data at least one region having a CT value within the second range of CT values.

The embodiments described herein facilitate determining whether a container includes contraband by processing scan data for the container using a first algorithm, identifying one or more regions of interest (ROIs), and processing the ROI(s) using a second algorithm.

BRIEF DESCRIPTION OF THE SEVERAL VIEWS OF THE DRAWINGS

FIG. 1 is a perspective view of a computed tomography (CT) scanning system.

FIG. 2 is a block diagram of the CT scanning system shown in FIG. 1.

FIG. 3 is a flowchart of an exemplary method for CT scanning that may be used with the CT scanning system shown in FIG. 1.

FIG. 4 is a flowchart of an exemplary method for CT based detection of contraband that may be used with the CT scanning system shown in FIG. 1.

DETAILED DESCRIPTION OF THE INVENTION

Figure 1:
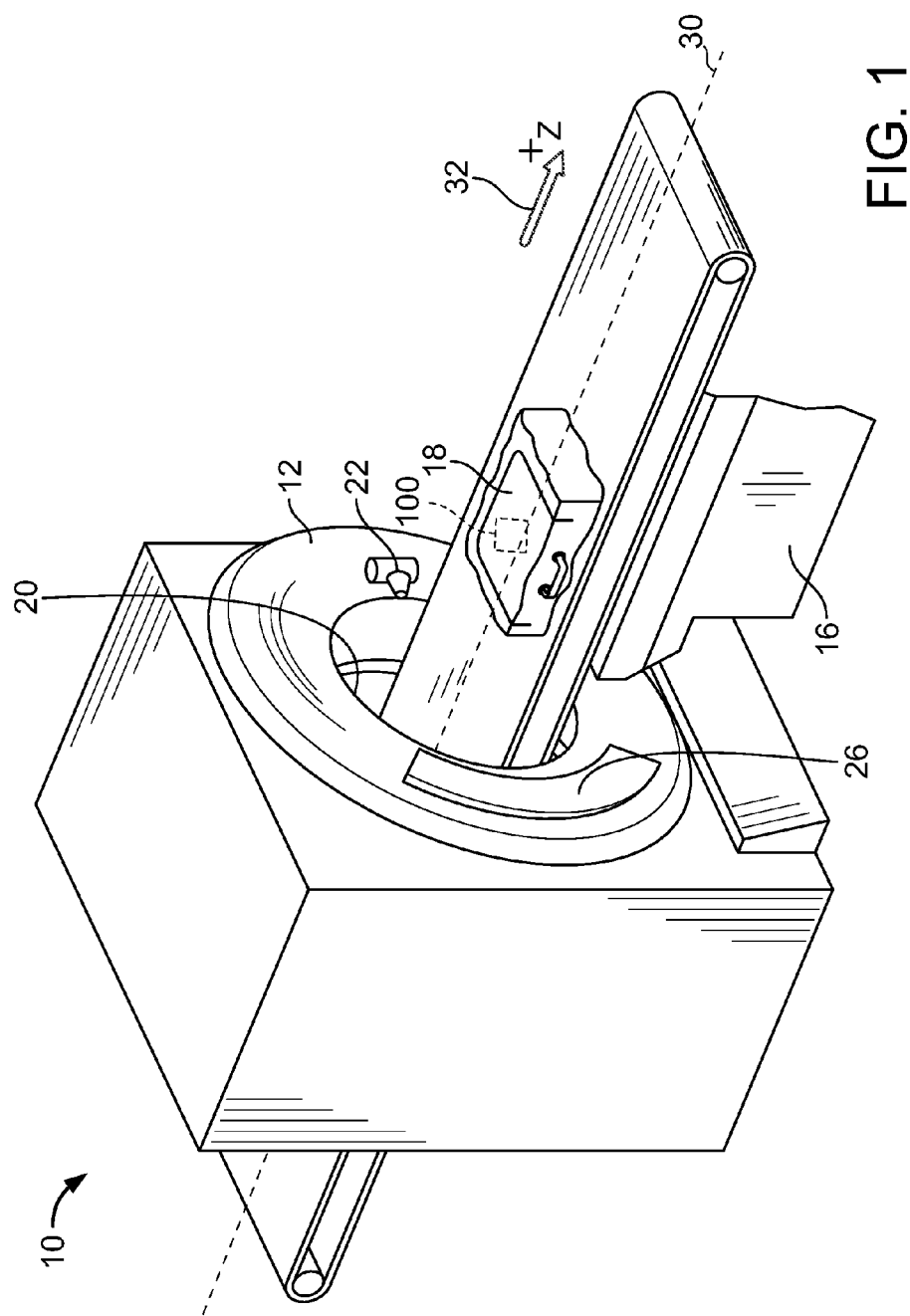
FIGS. 1-4 show exemplary embodiments of the systems and methods described herein.

Embodiments of the systems and methods described herein may use, for example, one CT value range or threshold for identifying regions of interest (ROIs) in CT scan data reconstructed with a high-speed algorithm, and another CT value range or threshold for identifying potential contraband in the ROIs, as reconstructed with a high-resolution algorithm. Accordingly, the embodiments described herein may detect explosives, such as thin sheet explosives, without substantially increasing a false alarm rate. More specifically, the embodiments described herein may facilitate increasing a ratio of detection rate to false alarm rate.

Further, embodiments described herein facilitate determining whether potential contraband is present within a container using a two-pass process. Because scan data is initially processed with a high-speed algorithm, and a region of interest (ROI) is identified in the output of the high-speed algorithm, a slower, high-quality algorithm may be used to process only the ROI. The embodiments thus provide the benefit of high-quality algorithm processing for critical portions of a container without imposing the cost of increased processing time for the entire container.

Moreover, the embodiments described herein facilitate producing improved imaging of a container by combining the output from a high-speed algorithm with the output from a high-quality algorithm. For example, imaging data from a high-quality (e.g., high-resolution) reconstruction may be overlaid on imaging data from a high-speed reconstruction. Imaging data may be partly or entirely composed of image elements. As used herein, the term "image element" refers to an element within an image, such as a pixel and/or a voxel.

While some embodiments are described in connection with a single ROI, the embodiments provided herein are operable with multiple ROIs. For example, two or more ROIs may be identified within data reconstructed using a high-speed algorithm. Scan data corresponding to each ROI may be reconstructed using a high-resolution algorithm to create a plurality of high-resolution data sets. The high-resolution data sets may be processed (e.g., inspected for CT values within a specified range, or combined with data reconstructed using the high-speed algorithm) individually or as a group.

A technical effect of the systems and methods described herein may include one or more of the following: (a) production of reconstructed data for an object using a first algorithm; (b) identification of a region of interest (ROI) within the reconstructed data; and (c) production of additional reconstructed data for a portion of the scan data corresponding to the ROI using a second algorithm. As used herein, the term "region of interest" (ROI) refers to a contiguous area or volume within reconstructed data. For example, an ROI may be defined as an area such as a circle, a square, a rectangle, or any other contiguous set of pixels within a "slice", or it may be defined as a volume such as a sphere, a cube, a rectangular prism, or any other contiguous set of voxels within three-dimensional data.

An ROI may be identified based on CT values. For example, in some embodiments, an ROI is identified by identifying an area within reconstructed data containing CT values above a predefined threshold or within a predefined range. In other embodiments, an ROI is identified by identifying an area within reconstructed data having a gradient of CT values exceeding a predefined slope threshold. For example, a slope threshold may be defined and CT values of neighboring image elements (e.g., pixels or voxels) compared to determine a rate of change (i.e., slope) in CT values. If the slope exceeds the slope threshold, the area containing the compared image elements is included in an ROI. Areas of the reconstructed data having a CT value gradient exceeding the slope threshold may appear in clusters or contiguous arrangements. Therefore, multiple areas may be consolidated into a single ROI. For example, a steep CT value gradient may be identified along the perimeter or outer surface of an object. The area or volume surrounding and/or containing the object may therefore be defined as a single ROI.

Embodiments described herein facilitate the detection of physical properties, such as one or more dimensions and/or a mass, of one or more objects within a container. In one example, an ROI is identified for an object in low-resolution reconstructed data from a first algorithm. A portion of the scan data corresponding to the ROI is reconstructed using a second algorithm to produce high-resolution reconstructed data. An approximate mass for the object is determined based the high-resolution reconstructed data. In another example, high-resolution reconstructed data is available for only a first portion of the object, and low-resolution reconstructed data is available for the remainder or the entirety of the object. A first partial mass is determined for the first portion of the object using the high-resolution reconstructed data. A second partial mass is determined for the remainder of the object using the low-resolution reconstructed data. The first partial mass and the second partial mass are added to determine a total approximate mass for the object.

Embodiments of the present invention described below are practicable in connection with a system for inspecting baggage. However, it should be apparent to those skilled in the art that the embodiments are likewise applicable to any suitable system for scanning containers including, without limitation, cargo containers, crates, boxes, drums, shipping containers, luggage, and suitcases, whether transported by water, land, and/or air, as well as other containers and/or objects.

Moreover, although the embodiments described below are in reference to an application in connection with and operation of a system incorporating an X-ray computed tomography (CT) scanning system for inspecting baggage, it should be apparent to those skilled in the art that any suitable radiation source including, without limitation, neutrons or gamma rays, may be used in alternative embodiments. Further, it should be apparent to those skilled in the art that any scanning system may be used that produces a sufficient number of pixels and/or voxels to enable the functionality of the methods and system described herein. For example, the system and methods described herein may be used for imaging or detecting critical portions in volumetric data in any other suitable application, such as, without limitation, medical imaging.

Figure 2:
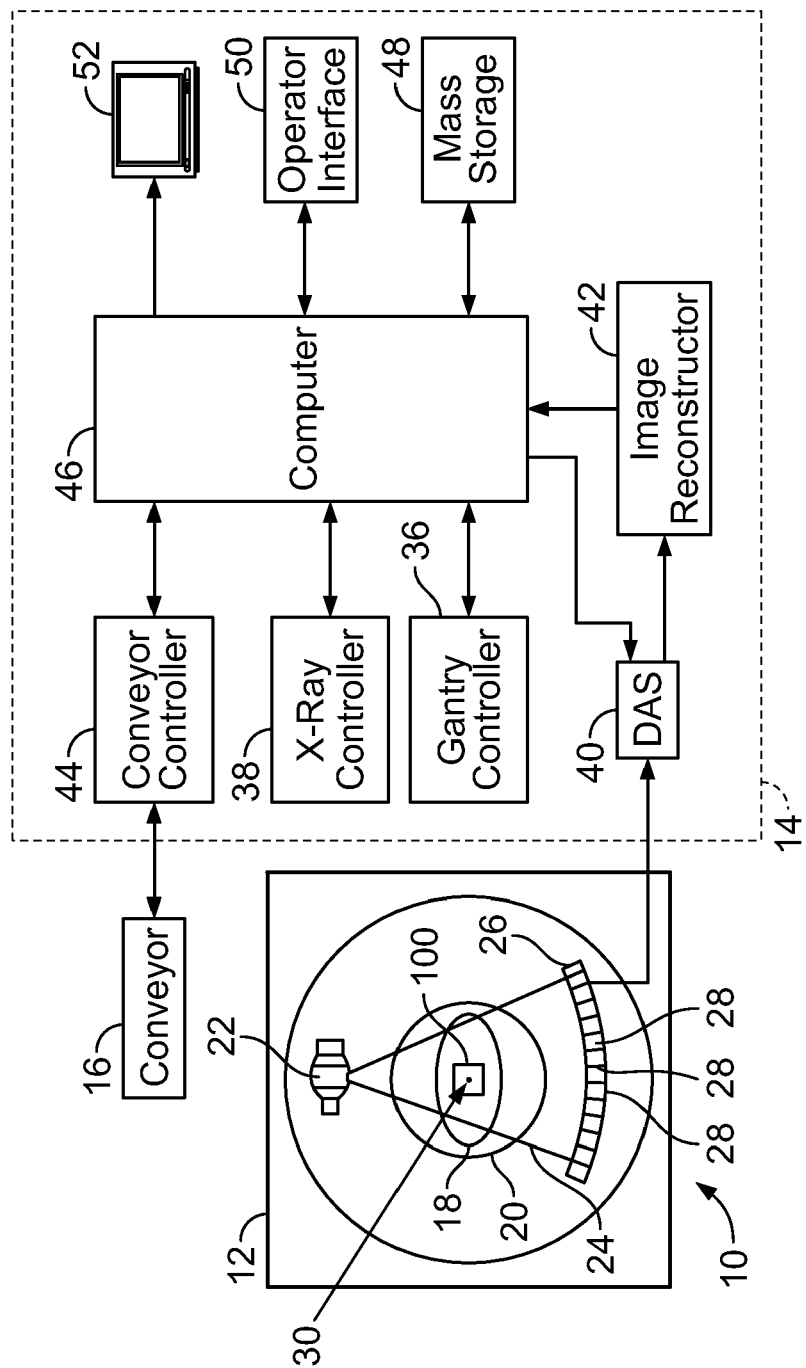

FIG. 1 is a perspective view of a computed tomography (CT) scanning system 10. FIG. 2 is a block diagram of CT scanning system 10. CT scanning system 10 includes a gantry 12, a control system 14, and a motorized conveyor belt 16 for positioning a container 18, such as a piece of luggage, in a gantry opening 20 defined through gantry 12. Gantry 12 includes an X-ray source 22 that projects a cone beam 24 of X-rays toward a detector array 26 opposing X-ray source 22 and coupled to gantry 12. X-ray source 22 is a radiation source and generates radiation, such as X-ray radiation. Detector array 26 is a detector and is formed by detector elements 28 that each detect radiation and produce a signal having a magnitude that represents, and is dependent on, the intensity of the attenuated X-ray beam after the X-ray beam has passed through container 18 being imaged. During a helical scan that acquires X-ray projection data, gantry 12 rotates X-ray source 22 and detector array 26 within a plane and about a center of rotation 30 of gantry 12. While gantry 12 is rotating, container 18 is transported through gantry 12 in a Z-direction 32, as shown in FIG. 1, that is perpendicular to the plane of rotation. In the exemplary embodiment, detector array 26 includes a plurality of detector rings each having a plurality of detector elements 28. The detector rings have an angular configuration corresponding to X-ray source 22.

Gantry 12 and X-ray source 22 are controlled by control system 14. Control system 14 includes a gantry controller 36, an X-ray controller 38, a data acquisition system (DAS) 40, an image reconstructor 42, a conveyor controller 44, a computer 46, a mass storage-system 48, an operator interface 50, and a display device 52. Gantry controller 36 controls a rotational speed and/or a position of gantry 12, and X-ray controller 38 provides power and timing signals to X-ray source 22. DAS 40 acquires analog data from detector elements 28 and converts the analog data to digital data for subsequent processing. Image reconstructor 42 receives the digitized X-ray data from DAS 40 and performs an image reconstruction process, including filtering the projection data using a helical reconstruction algorithm. Image reconstructor 42 may be configured to perform image reconstruction using multiple algorithms, either sequentially or simultaneously. For example, image reconstructor 42 may be configured to perform multi-slice reconstruction and cone beam reconstruction.

Computer 46 communicates with gantry controller 36, X-ray controller 38, and conveyor controller 44. More specifically, computer 46 transmits control signals to controllers 36, 38, and/or 44 and receives information from controllers 36, 38, and/or 44. Computer 46 is configured to provide commands and operational parameters to DAS 40 and to receive reconstructed image data from image reconstructor 42. The reconstructed image data is stored by computer 46 in mass-storage system 48 for subsequent retrieval. An operator interfaces with computer 46 through operator interface 50 that may include, without limitation, a keyboard, a graphical pointing device, a touch sensitive panel (e.g., a touch pad or touch screen), a stylus, and/or a mouse. The operator receives output, such as the reconstructed image, control settings, and/or any other suitable information, on display device 52. Display device 52 includes, for example, a cathode ray tube (CRT), a liquid crystal display (LCD), a light emitting diode (LED) display, an organic LED (OLED) display, a plasma display, a video projector, and/or any other device suitable for graphically rendering a reconstructed image, control settings, and/or other suitable information.

Operable communication between the various system elements shown in FIG. 2 is depicted by arrowhead lines that illustrate a path for signal communication and/or mechanical operation, depending on the system element involved. Operable communication amongst and/or between the system elements may be performed through a hardwired or a wireless network. Computer 46 can be a standalone computer or a network computer and can include instructions in a variety of computer languages for use on a variety of computer architectures, such as x86, x86-64, IA64, POWER, SPARC, and/or ARM, and under a variety of operating systems, such as MICROSOFT WINDOWS, MACOS, UNIX, LINUX, and/or any other suitable operating system. Other examples of computer 46 include, without limitation, a system having a microprocessor, a microcontroller, and/or any other suitable processing device capable of executing commands of computer readable data and/or a program for executing a control algorithm. In order to perform the methods described herein, as well as the computations therefore, such as the execution of Fourier analysis algorithm(s), and/or control processes described herein, any of the controllers described herein can include, but not be limited to, a processor(s), computer(s), memory, storage, register(s), timing, interrupt(s), communication interfaces, and/or input/output signal interfaces. For example, a controller includes input signal filtering to enable accurate sampling and conversion and/or acquisitions of such signals from communications interfaces. As described above, the embodiments described herein can be implemented through computer-implemented processes and apparatus for practicing those processes.

In operation, CT scanning system 10 acquires image data of container 18 by generating cone beam 24 using X-ray source 22, transmitting cone beam 24 through container 18, and receiving cone beam 24 at detector array 26 after the X-rays have been attenuated by container 18. More specifically, in the exemplary embodiment, CT scanning system 10 acquires image data of an object 100 within container 18 by receiving attenuated X-rays. Control system 14 receives data of the attenuated X-rays, as described above, and processes the received data as described herein.

In an exemplary embodiment, a CT control system such as control system 14 is provided for detecting contraband according to a first range of CT values and a second range of CT values. Control system 14 includes a data acquisition system (DAS) 40 configured to acquire, from detector array 26, scan data representing object 100. Control system 14 also includes image reconstructor 42, which is communicatively coupled to DAS 40 and configured to produce reconstructed data from the acquired scan data using a plurality of algorithms. For example, image reconstructor 42 may be configured to execute a multi-slice algorithm and/or a cone beam algorithm, though other algorithms are also contemplated. Control system 14 further includes computer 46, which is operatively coupled to image reconstructor 42. Computer 46 is configured to acquire from image reconstructor 42 a first set of reconstructed data produced from the acquired scan data using a first algorithm. Computer 46 is also configured to identify within the first set of reconstructed data at least one region having a CT value within the first range of CT values. Computer 46 is further configured to acquire from image reconstructor 42 a second set of reconstructed data corresponding to the at least one identified region. The second set of reconstructed data is produced from the acquired scan data using a second algorithm. Computer 46 is also configured to identify within the second set of reconstructed data at least one region having a CT value within the second range of CT values.

Control system 14 may be further configured to notify an operator of the at least one region having a CT value within the second range of CT values. For example, regions having a CT value within the second range may be graphically emphasized on display device 52 by computer 46.

In one embodiment, the first algorithm includes a multi-slice algorithm for high-speed reconstruction of the scan data, and the second algorithm includes a cone beam algorithm for accurate reconstruction of at least one ROI.

In some embodiments, control system 14 is further configured to combine the first set of reconstructed data with the second set of reconstructed data to generate an image (e.g., depicting at least a portion of object 100). For example, the second set of reconstructed data may be overlaid on the first set of reconstructed data to generate an image. The generated image may be presented to a user on display device 52.

In an exemplary embodiment, control system 14 is capable of performing method 300 and/or method 400, as described in more detail below. Method 300 and method 400 are described below as implemented on CT scanning system 10. However, method 300 and method 400 are not limited to implementation on CT scanning system 10. Rather, method 300 and method 400 may be embodied on a computer readable medium as a computer program and/or implemented and/or embodied by any other suitable means. The computer program may include a code segment that, when executed by a processor, configures the processor to perform one or more of the functions of method 300 and/or method 400. Further, method 300 and method 400 may also be used with pixels, voxels, and/or any suitable image element. Moreover, when more than one object 100 is present within a container, method 300 and method 400 can be performed for each object 100 within the container.

Figure 3:
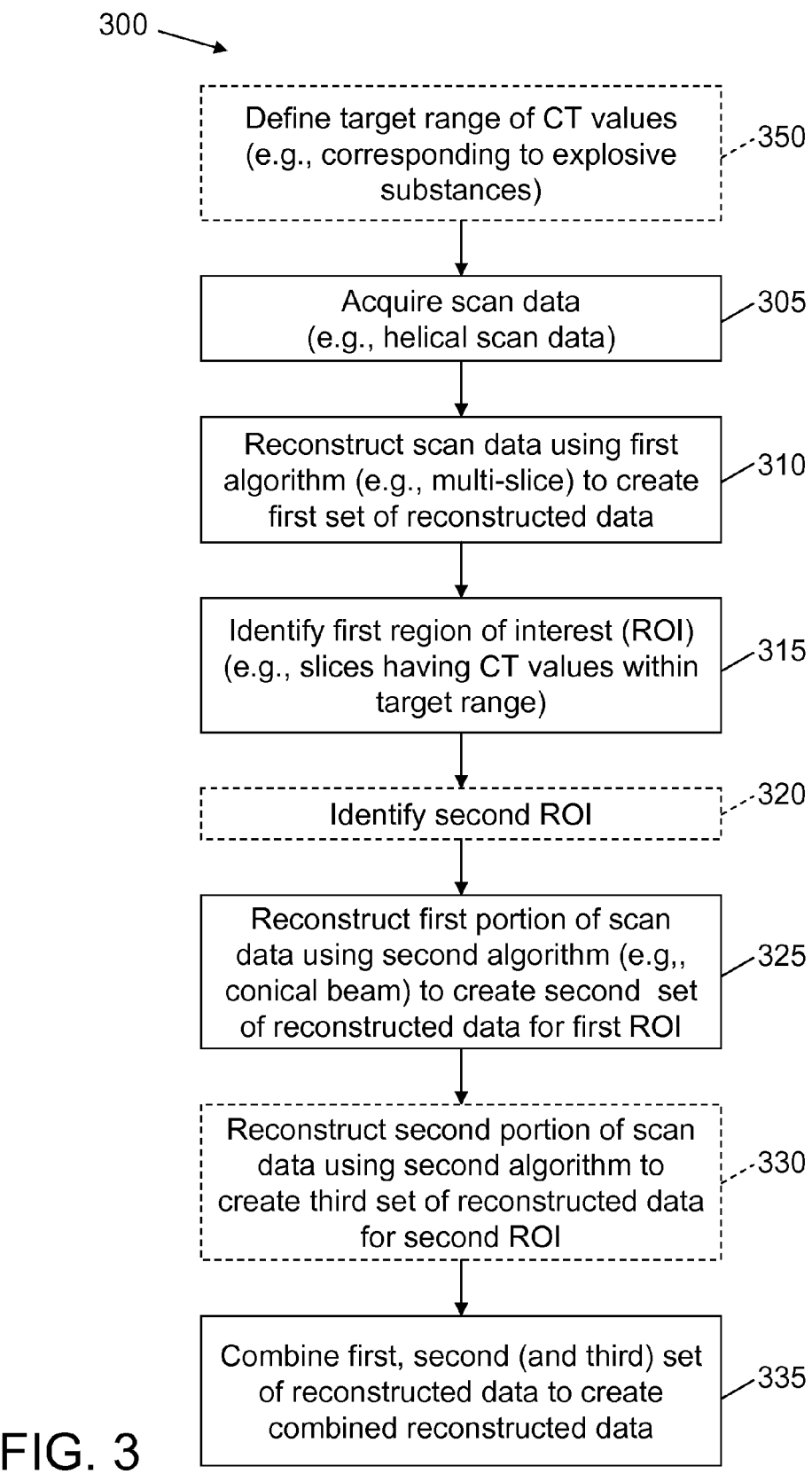

FIG. 3 is a flowchart of an exemplary method 300 for CT scanning that may be used with CT scanning system 10, shown in FIG. 1. In method 300, scan data, such as helical scan data, is acquired 305 from CT scanning system 10. The scan data is reconstructed 310 by a computer using a first algorithm to create a first set of reconstructed data. A first region of interest (ROI) is identified 315 within the first set of reconstructed data. One or more additional ROIs may also be identified 320 within the first set of reconstructed data. A portion of the scan data corresponding to the first ROI is reconstructed 325 by the computer using a second algorithm to create a second set of reconstructed data. If one or more additional ROIs are identified, a second portion of the scan data corresponding to the additional ROI(s) is reconstructed 330 by the computer using the second algorithm to create a third set of reconstructed data. The first set of reconstructed data and the second set of reconstructed data (and, if available, the third set of reconstructed data) are combined 335 by the computer to create combined reconstructed data.

In some embodiments, the second algorithm produces output having a higher resolution than the output of the first algorithm. For example, the first algorithm may be a multi-slice reconstruction algorithm, and the second algorithm may be a cone beam reconstruction algorithm.

In some embodiments, prior to acquiring 305 scan data, a target range of CT values is defined 350. The target range corresponds to contraband such as one or more explosive substances. The target range is used to identify 315 the first ROI and/or to identify 320 the additional ROI(s). In one embodiment, reconstructing 310 the scan data using the first algorithm includes using a multi-slice algorithm to produce a first set of reconstructed data including slices having CT values. A CT value may correspond to a density of a scanned object or a portion of a scanned object. For example, a CT value may vary directly with density. Identifying 315 and/or 320 an ROI includes identifying slices having at least one CT value within the target range.

Figure 4:
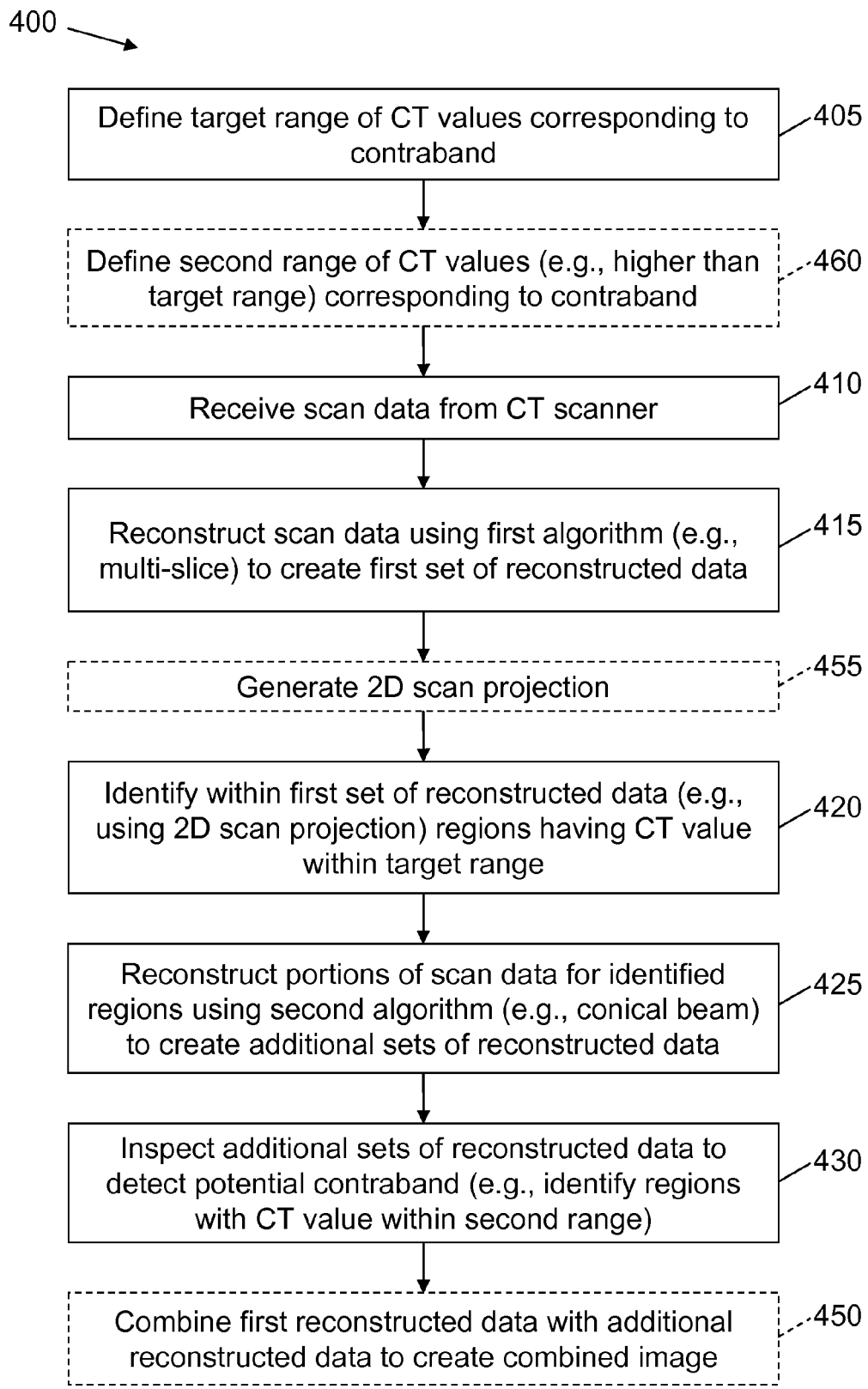

FIG. 4 is a flowchart of an exemplary method 400 for CT based detection of contraband that may be used with CT scanning system 10, shown in FIG. 1. A target range of CT values corresponding to contraband is defined 405. Scan data representative of object 100 is received 410 from CT scanning system 10 by a computer. The scan data is reconstructed 415 by the computer using a first algorithm to create a first set of reconstructed data. The first set of reconstructed data includes a plurality of regions having a plurality of CT values. CT values may correspond to (e.g., vary directly with) a density of a scanned object. At least one region having a CT value within the target range is identified 420 within the first set of reconstructed data. At least one portion of the scan data, each portion corresponding to one of the identified regions, is reconstructed 425 by the computer using a second algorithm to create at least one additional set of reconstructed data. Similar to the first set of reconstructed data, the at least one additional set of reconstructed data includes a plurality of regions having a plurality of CT values. The at least one additional set of reconstructed data is inspected 430 by the computer to detect a presence of potential contraband in object 100.

In some embodiments, the first set of reconstructed data is combined 450 with the at least one additional set of reconstructed data to create a combined image. Detected potential contraband may be indicated in the combined image by outlining, highlighting, color coding, labeling, and/or otherwise graphically distinguishing the potential contraband from other portions of the combined image.

In one embodiment, the second algorithm produces output having a higher resolution than the output of the first algorithm. For example, the first algorithm may be a multi-slice reconstruction algorithm, and the second algorithm may be a cone beam reconstruction algorithm.

In some embodiments, a two-dimensional (2D) scan projection is generated 455 by the computer from the first set of reconstructed data. Identifying 420 regions having a CT value within the target range includes identifying within the 2D scan projection at least one region having a CT value within the target range.

In addition to defining 405 the target range of CT values, a second range of CT values corresponding to contraband may be defined 460. The CT values in the second range may be higher than the CT values in the target range. If a second range of CT values is defined 460, inspecting 430 the at least one additional set of reconstructed data to detect a presence of potential contraband may include identifying within the at least one additional set of reconstructed data at least one region having a CT value within the second range.

The above-described methods and system for detecting contraband within a container facilitate reducing false alarm rates, as compared to methods and/or systems that apply only one algorithm to all objects identified within a container. More specifically, by applying a first algorithm generally, identifying a region of interest in the output of the first algorithm, and applying a second algorithm, different from the first algorithm, to the region of interest, the embodiments described herein more accurately identify contraband. Further, by more accurately and more efficiently identifying an object within a container, the embodiments described herein facilitate reducing a false negative rate, as compared to methods and/or systems that apply only one algorithm.

Exemplary embodiments of methods and a system are described above in detail. The methods and system are not limited to the specific embodiments described herein but, rather, components of the system and/or steps of the methods may be utilized independently and separately from other components and/or steps described herein. For example, the methods may also be used in combination with other imaging and/or detection systems and methods, and are not limited to practice with only the imaging system and/or the detection system and methods as described herein. Rather, the embodiments described herein can be implemented and utilized in connection with other image analysis applications.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for computed tomography (CT) scanning of an object, the method comprising:
    acquiring scan data representative of a scanned object from a CT scanning system;
    reconstructing the scan data by a computer using a multi-slice algorithm to create a first set of reconstructed data;
    identifying within the first set of reconstructed data a region of interest;
    reconstructing a portion of the scan data by the computer using a cone beam algorithm to create a second set of reconstructed data, the portion of the scan data corresponding to the region of interest; and
    combining the first set of reconstructed data and the second set of reconstructed data by the computer to create combined reconstructed data.

2. A method in accordance with claim 1, wherein receiving scan data comprises receiving helical scan data.

3. A method in accordance with claim 1, wherein the region of interest is a first region of interest, and the portion of the scan data is a first portion of scan data, the method further comprising:
    identifying within the first set of reconstructed data a second region of interest; and
    reconstructing a second portion of the scan data by the computer using the cone beam algorithm to create a third set of reconstructed data, the second portion of the scan data corresponding to the second region of interest,
    wherein the third set of reconstructed data is combined with the first set of reconstructed data and the second set of reconstructed data to create the combined reconstructed data.

4. A method in accordance with claim 1, further comprising:
    defining a target range of CT values;
    creating the first set of reconstructed data by defining a plurality of slices having a plurality of CT values; and
    identifying within the first set of reconstructed data a region of interest by identifying slices having at least one CT value within the target range of CT values.

5. A method in accordance with claim 4, wherein defining a CT value comprises defining a value varying directly with a density of a scanned object.

6. A method in accordance with claim 4, wherein defining a target range of CT values comprises defining a range of CT values corresponding to at least one explosive substance.

7. A method in accordance with claim 4, wherein the target range of CT values is a first target range of CT values, the method further comprising:
    defining a second target range of CT values; and
    identifying within the second set of reconstructed data at least one region having a CT value within the second target range of CT values.

8. A method in accordance with claim 1, wherein combining the first set of reconstructed data and the second set of reconstructed data comprises overlaying the second set of reconstructed data on the first set of reconstructed data.

9. A method for computed tomography (CT) based detection of contraband, the method comprising:
    defining a target range of CT values corresponding to contraband;
    receiving by a computer scan data representative of a scanned object from a CT scanning system;
    reconstructing by the computer the scan data using a first algorithm to create a first set of reconstructed data, the first set of reconstructed data comprising a plurality of regions having a plurality of CT values;
    identifying within the first set of reconstructed data at least one region having a CT value within the target range;
    reconstructing by the computer at least one portion of the scan data using a second algorithm to create at least one additional set of reconstructed data, each portion of the at least one portion corresponding to one region of the at least one identified region, the at least one additional set of reconstructed data comprising a plurality of regions having a plurality of CT values; and
    inspecting by the computer the at least one additional set of reconstructed data to detect a presence of potential contraband in the scanned object.

10. A method in accordance with claim 9, further comprising combining the first set of reconstructed data with the at least one additional set of reconstructed data to create a combined image.

11. A method in accordance with claim 9, wherein identifying within the first set of reconstructed data at least one region having a CT value within the target range comprises:
    by the computer, generating from the first set of reconstructed data a two-dimensional scan projection; and
    identifying within the two-dimensional scan projection at least one region having a CT value within the target range.

12. A method in accordance with claim 9, further comprising corresponding a CT value to a density of a portion of the scanned object.

13. A method in accordance with claim 9, wherein reconstructing the scan data using a first algorithm comprises reconstructing the scan data using a multi-slice algorithm.

14. A method in accordance with claim 13, wherein reconstructing at least one portion of the scan data using a second algorithm comprises reconstructing at least one portion of the scan data using a cone beam algorithm.

15. A method in accordance with claim 9, further comprising defining a second range of CT values corresponding to contraband, wherein inspecting the at least one additional set of reconstructed data comprises identifying within the at least one additional set of reconstructed data at least one region having a CT value within the second range.

16. A method in accordance with claim 15, wherein defining a second range of CT values comprises defining a range of CT values higher than the target range of CT values.

17. A computed tomography (CT) control system for detecting contraband according to a first range of CT values and a second range of CT values, the CT control system comprising:
- a data acquisition system (DAS) configured to acquire, from a detector array, scan data representing a scanned object;
- an image reconstructor communicatively coupled to the DAS and configured to produce reconstructed data from the acquired scan data using a plurality of algorithms; and
- a computer operatively coupled to the image reconstructor, the computer configured to:
  - acquire from the image reconstructor a first set of reconstructed data produced from the acquired scan data using a first algorithm;
  - identify within the first set of reconstructed data at least one region having a CT value within the first range of CT values;
  - acquire from the image reconstructor a second set of reconstructed data produced from the acquired scan data using a second algorithm, the second set of reconstructed data corresponding to the at least one identified region; and
  - identify within the second set of reconstructed data at least one region having a CT value within the second range of CT values.

18. A system in accordance with claim 17, wherein the computer is further configured to notify an operator of the at least one region having a CT value within the second range of CT values.

19. A system in accordance with claim 17, wherein the computer is further configured to combine the first set of reconstructed data with the second set of reconstructed data to generate an image.

20. A system in accordance with claim 17, wherein the first algorithm comprises a multi-slice algorithm, and the second algorithm comprises a cone beam algorithm.

* * * * *